United States Patent [19]

Merianos

[11] Patent Number: 5,252,320
[45] Date of Patent: Oct. 12, 1993

[54] PVP-HI-I₂ COMPLEXES HAVING A PARTITION COEFFICIENT ABOVE 300, AND PROCESS FOR MAKING SAME

[75] Inventor: John J. Merianos, Middletown, N.J.

[73] Assignee: ISP Investments Inc., Wilmington, Del.

[21] Appl. No.: 512,288

[22] Filed: Apr. 20, 1990

Related U.S. Application Data

[62] Division of Ser. No. 361,073, Jun. 5, 1989, abandoned.

[51] Int. Cl.⁵ .............................................. A61K 31/79
[52] U.S. Cl. .................................. 424/78.25; 424/667; 424/672; 525/355; 525/356
[58] Field of Search ....................... 424/80, 78.25, 667, 424/672; 525/355, 356

[56] References Cited

U.S. PATENT DOCUMENTS 3,177,114  4/1965  Cantor ................................... 424/79
4,575,491  3/1986  Pollack et al. ........................ 424/79

FOREIGN PATENT DOCUMENTS 993319  5/1961  United Kingdom .

*Primary Examiner*—Peter F. Kulkosky
*Attorney, Agent, or Firm*—Walter Katz; Marilyn J. Maue; Joshua J. Ward

[57] ABSTRACT

PVP-HI-I₂ complexes having a partition coefficient above 300 were prepared by oxidizing a PVP-HI intermediate in air and light at room temperature. These complex products were light in color, water soluble and stable.

8 Claims, No Drawings

PVP-HI-I$_2$ COMPLEXES HAVING A PARTITION COEFFICIENT ABOVE 300, AND PROCESS FOR MAKING SAME

This is a division of application Ser. No. 361,073, filed Jun. 5, 1989, now abandoned.

BACKGROUND OF THE INVENTION

1. Field of the Invention

This invention relates to polyvinylpyrrolidone-hydrogen iodide-iodine (PVP-HI-I$_2$) complexes, and to a process for making such complexes.

2. Description of the Prior Art

PVP-iodine has been used extensively in hospitals and elsewhere because of its germicidal, bactericidal, fungicidal and generally disinfecting properties. Usually it is sold as a brown powder, which contains about 10% available, or active iodine, and about 5% inactive iodine, in the form of iodide ion. The iodide ion is formed by reduction of iodine during preparation of the complex.

The partition coefficient of the complex, determined between an aqueous PVP-iodine solution and heptane, is a measure of the extent of bonding of iodine within the complex. A high partition coefficient value indicates a highly complexed iodine and little free iodine. Generally, known PVP-iodine complexes have partition coefficients of about 180 to 200. In complexes having a low partition coefficient, an iodine odor is perceptible from the complex and a moist potassium iodide starch paper introduced into the gas space above the PVP-iodine acquires a color, indicative of free iodine. Furthermore, aqueous solutions of PVP-iodine having a low partition coefficient are not very stable, i.e. they lose some available iodine upon storage.

Processes for making PVP-iodine complexes are disclosed in the following U.S. Pat. Nos.: 2,706,701; 2,739,922; 2,826,532; 2,900,305; 2,914,516; 3,028,300; 3,898,326; 4,027,083; 4,058,655; 4,094,967; 4,128,633; 4,200,710; 4,271,149; and 4,402,937. These prior art processes, however, are deficient in one or more respects, including poor complexation of iodine to PVP, and/or the requirement for excessive heating of the reactant components of the complex at elevated temperatures.

Accordingly, it is an object of the present invention to provide PVP-HI-I$_2$ complexes in which the iodine is very strongly bound, as evidenced by a partition coefficient which is above 300, and, preferably of 350 or more.

Another object is to provide a process for making PVP-HI-I$_2$ complexes having such exceptionally high partition coefficients, which process does not require extensive heating at elevated temperatures, and by which the complex is provided as a fine powder of light coloration.

These and other objects and features of the invention will be made apparent from the following more particular description of the ivnention.

SUMMARY OF THE INVENTION

In accordance with the invention, there is provided herein a stable PVP-HI-I$_2$ complex characterized by a partition coefficient of above 300, and, preferably 350 or more. The complex of the invention is a fine powder of light coloration.

The process of the invention comprises oxidizing a PVP-HI intermediate, suitably by oxygen, as provided by air, preferably in the presence of light, and, suitably at room temperature.

DETAILED DESCRIPTION OF THE INVENTION

This invention is based upon the discovery that PVP-HI-I$_2$ complexes having unusually high partition coefficients can be made by oxidizing a PVP-HI intermediate complex. Such oxidation is effected, for example, by oxygen, as furnished by air, at room temperature, and, preferably in the presence of light. Oxidation of the iodide ion in the PVP-HI intermediate furnishes the iodine component of the complex. The oxidation proceeds until the iodine:iodide ratio approaches 2:1. The partition coefficient of the complex is measured as being above 300, and generally 350 or more, and it is a lightly colored product. This coloration is indicative of a particular particle size of the complex rather than its iodine content. The iodine content in the complex generally is within the range of about 1-25% available iodine, preferably about 5-20%.

The starting material in the process of the invention is a PVP polymer, which is commercially available as a white powder of given molecular weight. Generally, the molecular weights of PVP polymers are given by their K-values, e.g., K-15 to K-90, representing molecular weights of 20,000 to 1,000,000. Preferably a PVP of K-30, which is relative to a molecular weight of about 40,000, is used.

The PVP starting material may be used herein as a powder, or a suspension of a powder in a liquid, for example, an organic liquid such as cyclohexane, or in the form of an aqueous or alcoholic solution. A sufficient amount of the PVP is made available in the process to provide a substantial excess over the 2 units required for complexation with HI and I$_2$, thus leaving considerable free PVP units available in the complex for water solubilization.

The first step in the process comprises reacting PVP with HI to form a PVP-HI complex in which 2 units of PVP are complexed with HI. The rest of the PVP units remain free for water solubilization. The HI reactant suitably may be introduced into PVP, present as a powder, suspension or solution, in the form of HI gas, or as an aqueous or alcoholic HI solution. Preferably sufficient agitation is provided to ensure complete reaction throughout the PVP. When a high level of iodine in the complex is desired, the HI reactant, e.g., in gaseous form, is added until the PVP is saturated with HI. When an aqueous or alcohol HI solution reactant is used, it is added slowly over a predetermined period, e.g., a couple of hours, suitably at room temperature, to form the desired PVP-HI complex.

At the conclusion of the reaction between PVP and gaseous HI, a yellow or brown colored PVP-HI powder is obtained which is isolated from the reaction mixture by filtration and washing. When an HI solution is used, the product is obtained by precipitation from an organic solvent, followed by filtration and drying.

The PVP-HI complex produced thereby suitably contains a minimum of about 3%, and up to 36% (saturation) by wt. HI, preferably about 15-25% HI. A small amount of I$_2$, generally about 0.3-2.5%, which is present in the HI reactant, also will appear in the intermediate complex.

In the process of the invention, the iodide ion in the PVP-HI complex then is oxidized to iodine, suitably by exposure to the oxygen of the air. This oxidation reaction may be carried out at room temperature, although higher and lower temperatures may be used. Preferably, such air oxidation occurs in the presence of light, such as the ultraviolet light of the ambient atmosphere, which light accelerates the oxidation reaction. Upon completion of the oxidation, a portion of the iodide ion is converted to iodine, preferably such that the ratio of iodine:iodide in the PVP-HI-$I_2$ complex approaches about 2:1. The product is a fine powder which is a lightly colored material.

Since oxidation is carried out at room temperature, the iodine formed is unusually tightly bound to the PVP, i.e. very little free iodine is present in the complex. Accordingly, the partition coefficient of the complex is much higher than related complexes made by other processes.

The partition coefficient of the complex, which is a measure of the degree of such iodine complexation, is determined in accordance with the description in U.S. Pat. No. 3,028,300. This procedure involves vigorously shaking 1.0 ml. of an aqueous PVP-HI-$I_2$ solution having an available iodine content of 1.0% with 25 ml. of heptane, for one minute, in a closed glass flask at 25° C. After standing for several minutes, the aqueous and heptane phases which form are separated. The iodine content of the aqueous phase is determined by titration with sodium thiosulfate and the iodine content in the heptane phase is determined spectrophotometrically. The partition coefficient (PC) of the complex is calculated from the following equation:

$$PC = \frac{\text{mg of iodine in aqueous phase}}{\text{mg of iodine in heptane phase}} \times \frac{\text{ml of heptane (25)}}{\text{ml of water (1)}}$$

According to this procedure, the partition coefficients of the PVP-HI-$I_2$ complex products of the invention were determined as being above 300, and usually about 350 or higher.

The invention will now be described by reference to the following examples:

EXAMPLE 1

A suspension of 50 g. of PVP-CI powder (K=30) (GAF Corp.) in 200 ml. of cyclohexane was reacted with gaseous HI over a couple of hours while stirring the suspension vigorously. A light yellow precipitate formed. The reaction product then was filtered and washed with cyclohexane. 65 g. of a complex of PVP with HI was obtained which was analyzed by sodium thiosulfate titration for $I_2$ content and by base titration to phenophthalein for HI content. The complex analyzed 23.15% HI and 0.63% iodine. The PVP:HI complex then was exposed to air and ambient light at room temperature. The complex turned dark brown as the HI in the complex was oxidized to $I_2$. After 6 hrs. the resultant PVP-HI-$I_2$ complex was isolated and analyzed again for iodine and iodide content. The HI content decreased to 8.5% while the $I_2$ content increased to 14.95%. The partition coefficient of the complex was measured as being 357.

EXAMPLE 2

The procedure of Example 1 was repeated using PVP powder in place of PVP suspended in cyclohexane. Gaseous HI was introduced until the HI content in the PVP-HI intermediate was 18.06% (0.62% iodine also was present). After a week of exposure to air and light at room temperature, the intermediate was converted to the desired PVP-HI-$I_2$ product. The complex analyzed 11.43% iodine and 7.35% HI. The partition coefficient of the complex was 356.

EXAMPLE 3

In a similar manner as in Example 2, using an aqueous solution of PVP in place of PVP powder, a PVP-HI intermediate having an HI content of 17.61% (and 0.32% was formed and a PVP-HI-$I_2$ product having 10.84% iodine and 5.98% HI was obtained. The partition coefficient of the product was 347.

EXAMPLE 4

Following Example 2, a PVP-HI intermediate having an HI content of 14.62% (and 0.42% iodine) and a PVP-HI-$I_2$ product having 9.37% iodine and 5.6% HI was obtained. The partition coefficient of the product was 325.

EXAMPLE 5

A solution of 120 g. of PVP-CI powder in 400 ml. of methanol was prepared and 225 g. (1 mole) of a 57% aqueous solution of HI was added slowly. Within a ½ hr. after addition was completed, the mixture turned black. Methanol then was removed by vacuum evaporation to give a viscous syrup, and acetone was added while stirring. A light burnt amber precipitate was formed which was filtered and dried in a vacuum evaporator. A fine powder was obtained which was analyzed as containing 24.19% HI (and 2.54% iodine). Upon exposure to air and light at room temperature for 6–8 hrs., followed by continued standing for a week, a PVP$_2$-HI-$I_2$ complex of light burnt amber color was formed. The complex contained 17.54% iodine and 8.37% HI. The partition coefficient was 369.

Although the invention has been described with reference to certain embodiments thereof, it will be understood that changes and modifications may be made which are within the skill of the art.

What is claimed is:

1. A process for preparing dry powders of a PVP-HI-$I_2$ complex which comprises (a) contacting PVP as a dry powder, suspension or solution thereof with HI in the form of a gas, or as an aqueous or alcoholic solution, to form a PVP-HI complex, and (b) oxidizing said PVP-HI in air to form said desired complex, and isolating the desired complex as a dry powder.

2. A process according to claim 1 wherein said oxidation is carried out in air and light.

3. A process according to claim 1 wherein said oxidation is effected at room temperature.

4. A process according to claim 1 wherein the PVP-HI complex has an HI content of about 3 to 36% by weight.

5. A process according to claim 4 wherein said HI content is about 15–25%.

6. A process according to claim 1 wherein the iodine:iodide ratio in the PVP-HI-$I_2$ complex is about 2:1.

7. A process according to claim 1 wherein the PVP-HI-$I_2$ complex has a partition coefficient of at least 300.

8. A process according to claim 1 wherein the available content in the PVP-HI-$I_2$ complex is about 1–25%.

* * * * *